US009901315B2

(12) United States Patent
Farbizio et al.

(10) Patent No.: US 9,901,315 B2
(45) Date of Patent: Feb. 27, 2018

(54) X-RAY SCATTER REDUCING DEVICE FOR USE WITH 2D MAMMOGRAPHY AND TOMOSYNTHESIS

(71) Applicants: Thomas Farbizio, Newtown, CT (US); Kenneth F. Defreitas, Patterson, NY (US); Ian Shaw, Yorktown Heights, NY (US)

(72) Inventors: Thomas Farbizio, Newtown, CT (US); Kenneth F. Defreitas, Patterson, NY (US); Ian Shaw, Yorktown Heights, NY (US)

(73) Assignee: Hologic, Inc., Marlborough, MA (US)

( * ) Notice: Subject to any disclaimer, the term of this patent is extended or adjusted under 35 U.S.C. 154(b) by 224 days.

(21) Appl. No.: 14/777,240

(22) PCT Filed: Mar. 13, 2014

(86) PCT No.: PCT/US2014/026572
§ 371 (c)(1),
(2) Date: Sep. 15, 2015

(87) PCT Pub. No.: WO2014/151856
PCT Pub. Date: Sep. 25, 2014

(65) Prior Publication Data
US 2016/0022230 A1    Jan. 28, 2016

Related U.S. Application Data

(60) Provisional application No. 61/790,336, filed on Mar. 15, 2013.

(51) Int. Cl.
A61B 6/02    (2006.01)
A61B 6/00    (2006.01)

(52) U.S. Cl.
CPC ............ *A61B 6/4291* (2013.01); *A61B 6/025* (2013.01); *A61B 6/502* (2013.01)

(58) Field of Classification Search
CPC ..... A61B 6/025; A61B 6/0414; A61B 6/4291; A61B 6/4435; A61B 6/4441; A61B 6/502; G01T 1/166
See application file for complete search history.

(56) References Cited

U.S. PATENT DOCUMENTS 7,123,684 B2 * 10/2006 Jing .......................... A61B 6/06
378/22
7,245,694 B2 * 7/2007 Jing ....................... A61B 6/025
378/37

(Continued)

OTHER PUBLICATIONS

International Search Report for International Application No. PCT/US2014/026572 dated Sep. 4, 2014 (3 page).

(Continued)

*Primary Examiner* — Thomas R Artman

(57) ABSTRACT

Systems and methods for reducing X-ray scatter during breast imaging, and more specifically during tomosynthesis imaging. In one embodiment, an anti-scatter grid having a plurality of septa may be configured to be positioned relative to an X-ray imaging device such that each septum of the plurality of septa extends along a direction substantially parallel to a coronal plane of a subject during imaging of the subject using the X-ray imaging device. The X-ray imaging device may be operable in a tomosynthesis mode for imaging of a breast of the subject and may include the anti-scatter grid disposed between a breast platform and the X-ray detector. The anti-scatter grid may be configured to move in a direction substantially parallel to a sagittal plane of the subject during tomosynthesis imaging.

18 Claims, 9 Drawing Sheets

(56) References Cited

U.S. PATENT DOCUMENTS

| | | | |
|---|---|---|---|
| 7,418,076 B2 | 8/2008 | Li | |
| 7,430,272 B2* | 9/2008 | Jing | A61B 6/06 378/21 |
| 7,443,949 B2* | 10/2008 | Defreitas | A61B 6/0414 378/208 |
| 7,583,786 B2* | 9/2009 | Jing | A61B 6/025 378/37 |
| 7,715,524 B2* | 5/2010 | Yamakita | A61B 6/502 378/154 |
| 7,760,853 B2* | 7/2010 | Jing | A61B 6/06 378/21 |
| 7,831,296 B2* | 11/2010 | DeFreitas | A61B 6/502 378/37 |
| 7,869,563 B2* | 1/2011 | Defreitas | A61B 6/502 378/114 |
| 7,881,428 B2* | 2/2011 | Jing | A61B 6/025 378/37 |
| 7,949,091 B2* | 5/2011 | Jing | A61B 6/06 378/37 |
| 8,175,219 B2* | 5/2012 | Defreitas | A61B 6/502 378/189 |
| 8,217,357 B2* | 7/2012 | Stein | A61B 6/025 250/366 |
| 8,416,915 B2* | 4/2013 | Jing | A61B 6/06 378/21 |
| 8,452,379 B2* | 5/2013 | DeFreitas | A61B 6/502 378/37 |
| 8,565,372 B2* | 10/2013 | Stein | A61B 6/025 378/116 |
| 8,565,374 B2* | 10/2013 | Defreitas | A61B 6/502 378/21 |
| 8,571,174 B2* | 10/2013 | Smith | A61B 6/025 378/37 |
| 8,592,772 B2* | 11/2013 | Stein | A61B 6/025 250/363.04 |
| 8,744,041 B2* | 6/2014 | Smith | A61B 6/025 378/37 |
| 8,831,171 B2* | 9/2014 | Jing | A61B 6/06 378/21 |
| 8,942,343 B2* | 1/2015 | Smith | A61B 6/025 378/37 |
| 9,020,579 B2* | 4/2015 | Smith | A61B 6/025 600/427 |
| 9,066,706 B2* | 6/2015 | DeFreitas | A61B 6/502 |
| 9,241,681 B2* | 1/2016 | Smith | A61B 6/025 |
| 9,498,175 B2* | 11/2016 | Stein | A61B 6/025 |
| 9,498,176 B2* | 11/2016 | Smith | A61B 6/025 |
| 9,549,709 B2* | 1/2017 | DeFreitas | A61B 6/502 |
| 2004/0101095 A1* | 5/2004 | Jing | A61B 6/06 378/37 |
| 2005/0063509 A1* | 3/2005 | Defreitas | A61B 6/0414 378/37 |
| 2005/0113681 A1* | 5/2005 | DeFreitas | A61B 6/502 600/426 |
| 2007/0030949 A1* | 2/2007 | Jing | A61B 6/06 378/37 |
| 2007/0036265 A1* | 2/2007 | Jing | A61B 6/025 378/37 |
| 2007/0076844 A1* | 4/2007 | Defreitas | A61B 6/0414 378/37 |
| 2007/0242800 A1* | 10/2007 | Jing | A61B 6/025 378/37 |
| 2008/0112534 A1* | 5/2008 | Defreitas | A61B 6/0414 378/37 |
| 2009/0003519 A1* | 1/2009 | Defreitas | A61B 6/502 378/37 |
| 2009/0010384 A1* | 1/2009 | Jing | A61B 6/06 378/37 |
| 2009/0041183 A1* | 2/2009 | Yamakita | A61B 6/502 378/37 |
| 2009/0213987 A1* | 8/2009 | Stein | A61B 6/025 378/37 |
| 2009/0304147 A1* | 12/2009 | Jing | A61B 6/025 378/37 |
| 2010/0135456 A1* | 6/2010 | Jing | A61B 6/06 378/22 |
| 2010/0260316 A1* | 10/2010 | Stein | A61B 6/025 378/37 |
| 2010/0261997 A1* | 10/2010 | Ren | A61B 6/037 600/424 |
| 2011/0069808 A1* | 3/2011 | DeFreitas | A61B 6/502 378/5 |
| 2011/0069809 A1* | 3/2011 | Defreitas | A61B 6/502 378/7 |
| 2011/0087132 A1* | 4/2011 | DeFreitas | A61B 90/11 600/567 |
| 2011/0216879 A1* | 9/2011 | Jing | A61B 6/06 378/22 |
| 2012/0063566 A1* | 3/2012 | Smith | A61B 6/025 378/37 |
| 2012/0063567 A1* | 3/2012 | Smith | A61B 6/025 378/37 |
| 2012/0170711 A1* | 7/2012 | Souchay | A61B 6/06 378/37 |
| 2012/0195403 A1 | 8/2012 | Vedantham et al. | |
| 2012/0219111 A1* | 8/2012 | Defreitas | A61B 6/502 378/37 |
| 2012/0238870 A1* | 9/2012 | Smith | A61B 6/025 600/431 |
| 2012/0250969 A1* | 10/2012 | Stein | A61B 6/025 382/131 |
| 2012/0263273 A9* | 10/2012 | Stein | A61B 6/025 378/37 |
| 2013/0223591 A1* | 8/2013 | Jing | A61B 6/06 378/37 |
| 2013/0272494 A1* | 10/2013 | DeFreitas | A61B 6/502 378/37 |
| 2014/0044230 A1* | 2/2014 | Stein | A61B 6/025 378/37 |
| 2014/0044231 A1* | 2/2014 | DeFreitas | A61B 6/502 378/37 |
| 2014/0341337 A1* | 11/2014 | Smith | A61B 6/025 378/37 |
| 2014/0376690 A1* | 12/2014 | Jing | A61B 6/06 378/22 |
| 2015/0049859 A1* | 2/2015 | DeFreitas | A61B 6/502 378/20 |
| 2015/0148670 A1* | 5/2015 | Smith | A61B 6/025 600/427 |
| 2015/0327826 A1* | 11/2015 | Smith | A61B 6/025 600/425 |
| 2016/0022230 A1* | 1/2016 | Farbizio | A61B 6/025 378/22 |
| 2016/0113606 A1* | 4/2016 | Smith | A61B 6/025 600/411 |
| 2016/0235380 A1* | 8/2016 | Smith | A61B 6/025 |
| 2016/0270742 A9* | 9/2016 | Stein | A61B 6/025 |
| 2017/0065238 A1* | 3/2017 | Smith | A61B 6/025 |
| 2017/0128028 A1* | 5/2017 | DeFreitas | A61B 6/4417 |
| 2017/0135650 A1* | 5/2017 | Stein | A61B 6/025 |

OTHER PUBLICATIONS

International Written Opinion for International Application No. PCT/US2014/026572 dated Sep. 4, 2014 (9 page).

International Preliminary Report on Patentability for International Application No. PCT/US2014/026572 dated Sep. 15, 2014 (5 page).

\* cited by examiner

X-RAY SCATTER REDUCING DEVICE FOR USE WITH 2D MAMMOGRAPHY AND TOMOSYNTHESIS

CROSS-REFERENCE TO RELATED APPLICATIONS

The present application is a National Stage of PCT/US2014/026572, filed 13 Mar. 2014, which claims the benefit under 35 U.S.C. § 119 to U.S. Provisional Patent Application Ser. No. 61/790,336, filed Mar. 15, 2013 and which applications are incorporated herein by reference. To the extent appropriate, a claim of priority is made to each of the above disclosed applications.

FIELD OF THE INVENTION

The present invention generally relates to radiography and more specifically to anti-scatter devices and methods of reducing X-ray scatter for breast imaging.

BACKGROUND

X-ray mammography systems are widely used for breast imaging. More recently, advanced imaging systems based on tomosynthesis have been developed for use in screening of breast cancer and other lesions. Tomosynthesis systems are three-dimensional (3D) mammography systems that allow high resolution breast imaging based on limited angle tomography at mammographic X-ray dose levels. In contrast to typical two-dimensional (2D) mammography systems, a tomosynthesis system acquires a series of X-ray projection images, each projection image obtained at a different angular displacement as the X-ray source moves along a path, such as a circular arc, over the breast. In contrast to conventional computed tomography (CT), tomosynthesis is typically based on projection images obtained at limited angular displacements of the X-ray source around the breast. Tomosynthesis reduces or eliminates the problems caused by tissue overlap and structure noise present in 2D mammography imaging. Digital breast tomosynthesis also offers the possibility of reduced breast compression, improved diagnostic and screening accuracy, fewer recalls, and 3D lesion localization.

Scattered X-rays generally cause blur and degrade the quality of X-ray images. Anti-scatter grids are typically used in conventional 2D X-ray imaging systems to reduce X-ray scatter by selectively blocking scattered X-rays, such as Compton scattered X-rays, while allowing primary X-rays to reach the X-ray detector. Thus, an anti-scatter grid enhances image quality and tissue contrast by reducing the number of detected X-rays that have been scattered by tissue. While anti-scatter grids have been developed for use in conventional X-ray imaging systems, such as 2D mammography, there is a need for X-ray scatter reducing devices and methods that work with tomosynthesis imaging.

SUMMARY

Aspects and embodiments of the present disclosure are directed to providing systems and methods of reducing X-ray scatter for breast imaging, and more particularly for tomosynthesis imaging. Anti-scatter grids and X-ray imaging systems having anti-scatter grids incorporated therein are disclosed. In various embodiments, an X-ray imaging system may have an anti-scatter grid configured according to aspects disclosed herein and may be operable in at least one of a 2D mammography mode and a (3D) tomosynthesis mode. The use of an anti-scatter grid is particularly helpful for imaging a thick breast, for example a heterogeneously dense or an extremely dense breast.

Various aspects, embodiments, and advantages are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment. Features and advantages discussed in connection with any one or more embodiments according to one or more aspects are not intended to be excluded from a similar role in any other embodiment or aspect.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures.

DETAILED DESCRIPTION

Figure 1A:
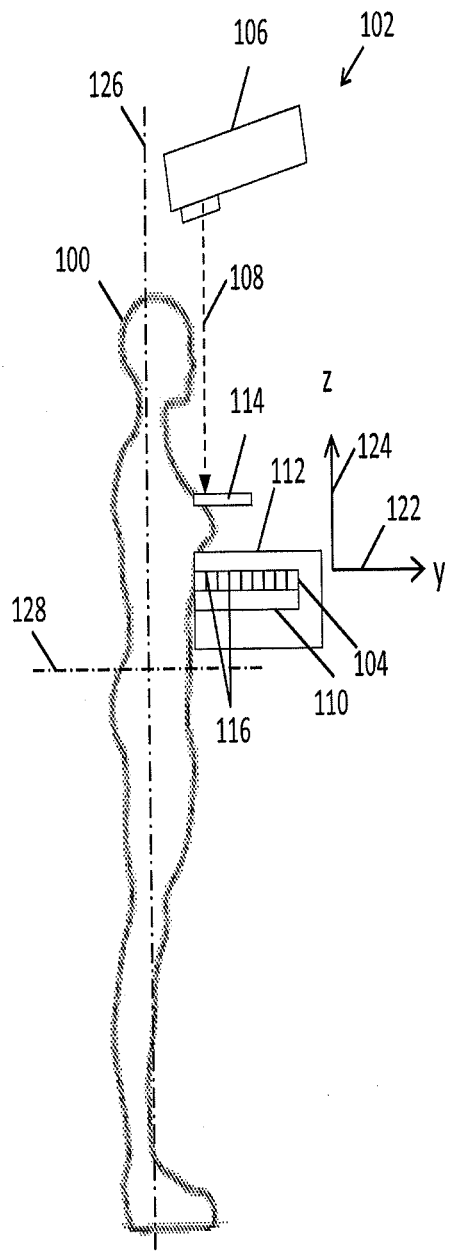
FIG. 1A is a cross-sectional view illustrating imaging a breast of a subject using one embodiment of a tomosynthesis imaging apparatus having an anti-scatter grid configured according to aspects of the present invention.

Anti-scatter grids are often used in radiographic imaging to reduce the image degrading effects of scattered radiation on the image. Stationary anti-scatter grids can cause Moire pattern artifacts that are especially troublesome in a digital X-ray detector, for example due to the interference of the anti-scatter grid pattern with the pixel pattern of the X-ray detector. Thus, the resulting image exhibits Moire patterning or grid line artifacts that degrade image quality. Nonlimiting examples of anti-scatter grids for use in radiographic imaging include U.S. Patent Application Publication No. 2012/0170711 and U.S. Pat. Nos. 7,418,076 and 7,715,524, each of which is incorporated by reference herein in their entireties.

Aspects and embodiments of the present disclosure are directed to providing X-ray scatter reducing systems and methods that also allow the reduction or correction of Moire patterns for use in 2D and 3D mammography. In some embodiments, the anti-scatter grid may move relative to the X-ray detector, during X-ray exposure, to blur out Moire patterns. In various embodiments, Moire patterns may also be reduced by using image processing techniques.

According to one aspect of the present disclosure, it is appreciated that motion of the anti-scatter grid presents unique challenges for use in tomosynthesis imaging systems, which have hindered the use of anti-scatter grids for tomosynthesis imaging. For example, the motion of the anti-scatter grid must be synchronized with the X-ray exposure signal. However, in contrast with conventional 2D mammography, tomosynthesis imaging involves obtaining multiple X-ray projection images of the breast, each of the X-ray projection images obtained during a short X-ray exposure time at each of multiple angular displacements of the X-ray source relative to the breast. Therefore, the anti-scatter grid must move a distance effective to reduce Moire patterns during very short time durations corresponding to X-ray exposures of tomosynthesis imaging. Furthermore, tomosynthesis imaging systems typically impose tight spatial constraints on the distance that the anti-scatter grid may move during imaging.

Various aspects and embodiments presented herein address the challenges described above. In various embodiments, an anti-scatter grid includes thin strips, also referred to as septa or laminae. The septa may be made of a radio-opaque material or a highly X-ray absorbing material, such as lead, and may be separated by interspaces. Interspaces may be made of a radiolucent material or a low X-ray attenuating material such as carbon fiber or aluminum. In contrast to conventional anti-scatter grids, embodiments of anti-scatter grids disclosed herein may be configured to be positioned relative to an X-ray imaging device, and more particularly a tomosynthesis imaging device, such that each septum of the anti-scatter grid is oriented lengthwise along an axis that is substantially parallel to the coronal plane of the subject during imaging. In some embodiments, the anti-scatter grid may be configured to move along a direction substantially parallel to a sagittal plane of the subject during imaging. In some embodiments, the anti-scatter grid may have a septa density, also referred to as grid line density, of at least 70 septa per cm, in contrast to conventional anti-scatter grids which typically have septa density in the range of 30 to 50 septa per cm. The various embodiments disclosed herein allow the anti-scatter grid to move a relatively short distance compared to conventional anti-scatter grids, in durations synchronized with the X-ray exposures of tomosynthesis imaging, and in orientations configured to reduce Moire patterns in the resulting images.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

It is to be appreciated that for simplicity and clarity of illustration, where considered appropriate, reference numerals may be repeated among the figures to indicate corresponding or analogous elements or steps.

Turning now to the drawings, FIG. 1A illustrates a cross-sectional side view of imaging a breast of a subject 100 using a tomosynthesis imaging apparatus 102 having an anti-scatter grid 104 configured according to aspects of the present disclosure. In some embodiments, the tomosynthesis imaging apparatus 102 may further be operable in a 2D mammography mode, as described for example in the patent documents U.S. Pat. No. 7,831,296, US 2011/0216879 and US 2012/0219111, which are hereby incorporated by reference in their entireties.

The tomosynthesis imaging apparatus 102 includes an X-ray source 106, also referred to as an X-ray tube. The X-ray source 106 is configured to deliver an X-ray beam towards the breast of the subject 100 as indicated for example by line 108. In 2D mammography mode, the X-ray source may direct the X-ray beam during an X-ray exposure from a fixed position. In tomosynthesis mode, the X-ray source may move along a path such as an arc above the breast of the subject 100, as illustrated and described further below with reference to FIGS. 4A to 4C. The tomosynthesis imaging apparatus 102 further includes an X-ray detector 110 positioned to receive the X-rays transmitted through the breast being imaged. In some embodiments, the detector may be a digital X-ray detector. In 2D mammography imaging, the X-ray detector 110 may be stationary. In tomosynthesis mode, the X-ray detector 110 may move or rotate along a path that is reciprocal to the motion of the X-ray source 106, thereby maintaining its orientation towards the X-ray source, as illustrated and described further below with reference to FIGS. 4A to 4C.

The tomosynthesis imaging apparatus 102 further includes a platform 112 configured to position the breast of the subject 100 between the X-ray source 106 and the X-ray detector 110. The platform 112 is positioned between the X-ray source 106 and the X-ray detector 110 and remains stationary as at least one of the X-ray source and the X-ray detector rotates around the platform during tomosynthesis imaging of the breast of the subject 100. The tomosynthesis imaging apparatus 102 further includes an immobilization structure 114 configured to compress and immobilize the breast for imaging. The breast may be compressed to reduce motion of the subject and also to reduce scatter, separate overlapping structures in the breast, make the thickness of the imaged breast more uniform, and to provide more uniform X-ray exposure. While the platform 112 and the immobilization structure 114 have been described as separate elements with reference to FIG. 1A, the platform and the immobilization structure may be provided as an integrated element.

FIG. 1A further illustrates the body planes of the subject 100. The cross-sectional view of the subject 100 in FIG. 1A is in a plane parallel to the sagittal plane of the subject. The sagittal plane is a longitudinal plane that divides the subject 100 into right and left parts. The sagittal plane is parallel to the y-z plane which includes the y-axis 122 and the z-axis 124 as shown in FIG. 1A. The x-axis (not shown in FIG. 1A, but shown and described further below with reference to FIGS. 4B and 4C) extends out of the page and is orthogonal to the y-z plane. The coronal plane 126 of the subject 100 is another longitudinal plane that divides the subject into front and back parts. The coronal plane 126, indicated by a dashed line in FIG. 1A, is parallel to the x-z plane which includes the z-axis 124 and the x-axis. The transverse plane 128 of the subject 100 is a horizontal plane that divides the subject into upper and lower parts. The transverse plane 128, indicated by a dashed line in FIG. 1A, is parallel to the x-y plane which includes the y-axis 122 and the x-axis. The sagittal plane, the coronal plane 126 and the transverse plane 128 are mutually orthogonal and parallel to the y-z plane, the x-z plane and the x-y plane respectively.

References to body planes are used herein to describe the orientation and motion of anti-scatter grids. It is to be appreciated that an anti-scatter grid may be fixed relative to the position of an arm of the X-ray imaging apparatus and the anti-scatter grid motion may be described based on the Cartesian coordinates of the arm which may be positioned relative to the body planes.

The tomosynthesis imaging apparatus 102 includes the anti-scatter grid 104 having a plurality of septa 116. The anti-scatter grid 104 has a septa density of at least 70 septa per cm. The anti-scatter grid 104 is positioned between the platform 112 and the X-ray detector 110 and is configured to reduce X-rays scattered by the breast tissue from reaching the X-ray detector 110 during imaging. The anti-scatter grid 104 is positioned relative to the tomosynthesis imaging apparatus 102 such that each septum 116 of the plurality of septa extends along a direction substantially parallel to the coronal plane 126 (or the x-z plane). In an embodiment, the plurality of septa may be exactly parallel to the coronal plane, slightly off-angle to (but generally in the plane of) the coronal plane, or some combination thereof. For purposes of illustration, as an example, the septa closest to the chest wall of the patient may be exactly parallel to the coronal lane while septa farthest from the chest wall may be slightly off-angle to (but generally in the plane of) the coronal plane. In another example, the septa closest to the chest wall of the patient may be slightly off-angle to (but generally in the plane of) the coronal plane while septa farthest from the chest wall may exactly parallel to the coronal plane. FIG. 1A shows a side view of the septa 116, illustrating the height and thickness of the septa. However, the septa 116 have lengths that extend along axes parallel to the coronal plane 126, as illustrated and described further below with reference to FIG. 3A. For breast imaging, the orientation of the septa 116 along a direction substantially parallel to the coronal plane 126 may correspond to the septa being substantially parallel to the chest wall of the subject 100. The configuration of the septa to extend lengthwise along a direction substantially parallel to the coronal plane 126 maximizes transmission through the anti-scatter grid during tomosynthesis imaging. In an embodiment, the septa are focused to the X-ray source, e.g., such that septa closest to the chest wall may not have the same alignment as septa farthest from the chest wall. Additionally or alternatively, the septa at the top surface of the anti-grid 104 are generally parallel to one another.

Figure 1B:
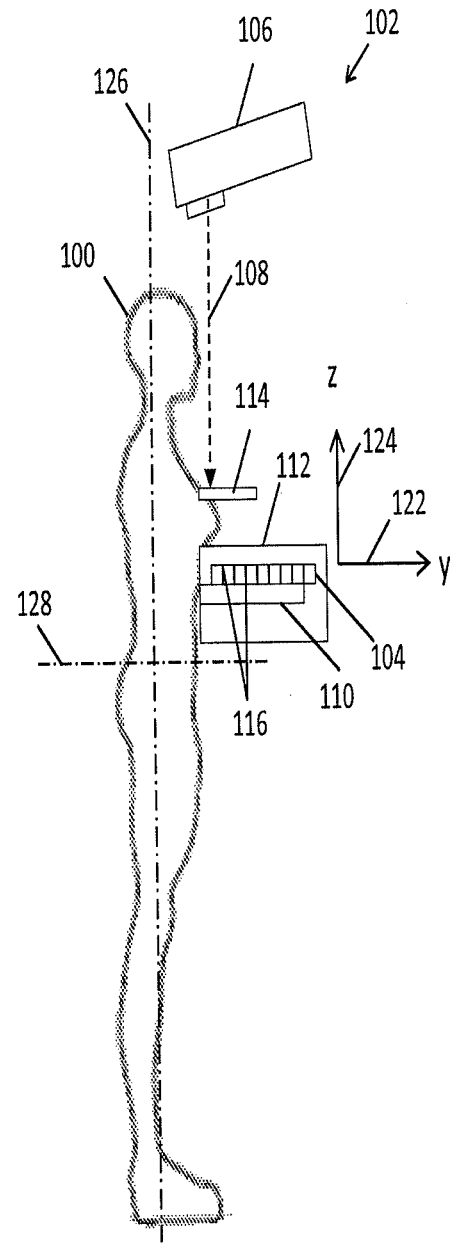
FIG. 1B shows the same embodiment as FIG. 1A, further illustrating a movement of the anti-scatter grid along a direction parallel to the sagittal plane of the subject according to aspects of the present invention.

FIG. 1B shows the same embodiment for imaging the breast of the subject 100, further illustrating movement of the anti-scatter grid 104. As shown, the anti-scatter grid has moved relative to the X-ray detector 110. The anti-scatter grid 104 moves along a direction substantially parallel to the sagittal plane (or the y-z plane). As described above, motion of the anti-scatter grid relative to the X-ray detector allows reducing Moire patterns in the resulting images. In various embodiments, motion of the anti-scatter grid along a direction substantially parallel to the sagittal plane maximizes the blurring of grid lines (Moire patterns) and reduces the intensity of the grid lines.

While the X-ray detector 110 may be stationary during some imaging modes, the X-ray detector may move to maintain its orientation towards the X-ray source as the X-ray source moves during tomosynthesis imaging. The motion of the anti-scatter grid 104 may further be coupled to the motion of the X-ray detector 110. For example, the anti-scatter grid 104 may be rigidly attached to the X-ray detector 110. Thus, the anti-scatter grid may move along with the X-ray detector when the X-ray detector moves. For example, during tomosynthesis imaging, the anti-scatter grid may move or rotate with the X-ray detector to maintain its orientation towards a focal spot of the X-ray source 106, while simultaneously moving relative to the X-ray detector to reduce Moire patterns. In various embodiments, the anti-scatter grid 104 may be moving along with the X-ray detector 110 while the septa 116 maintain their orientation along a direction substantially parallel to the coronal plane 126. For example, the X-ray detector 110 along with the anti-scatter grid 104 may rotate around an axis parallel to the y-axis 122 (as shown for example in FIG. 4C) while the septa 116 maintain a lengthwise direction that is parallel to the coronal plane 126. In other embodiments, the anti-scatter grid may not move or rotate with the X-ray detector. In yet other embodiments, the anti-scatter grid may be stationary during tomosynthesis imaging. For example, the anti-scatter grid may be coupled to a stationary platform.

The anti-scatter grid 104 is further configured to move along a second direction that is substantially parallel to the coronal plane 126 of the subject 100 during imaging. In various embodiments, the anti-scatter grid may move along at least one of a first direction that is substantially parallel to the sagittal plane of the subject 100 and a second direction that is substantially parallel to the coronal plane 126. For example, motion of the anti-scatter grid along the x-axis in conjunction with motion along the y-axis enables circular and/or elliptical motion. In the case where the septa are slightly off parallel with the chest wall (coronal plane), circular motion or elliptical motion may further blur the grid lines and reduce Moire patterns.

The anti-scatter grid 104 may move along a trajectory that allows reducing Moire patterns in the resulting images. The motion trajectory of the anti-scatter grid may be linear, circular or elliptical. Furthermore, the anti-scatter grid 104 may move at a velocity effective to reduce Moire patterns during tomosynthesis imaging. Velocity profiles may minimize velocity variations of anti-scatter grids, thereby reducing grid lines. The velocity profile may be one of a sinusoidal profile and a trapezoidal profile. A sinusoidal profile may simplify the motion algorithm. For example, a rotary motor as shown and described further below with reference to FIG. 5 may be used to provide a sinusoidal profile. The constant velocity of a rotary motor shaft may produce a sinusoidal profile, for example in the direction of the x-axis and/or the y-axis. A trapezoidal profile may be more effective at blurring grid lines compared to a sinusoidal profile. However, a trapezoidal profile may be difficult to employ in a rotary motor and may instead be provided by a linear motor as shown and described further below with reference to FIG. 6. The motion of the anti-scatter grid 104 may be synchronized with the X-ray exposures during tomosynthesis imaging, such that the anti-scatter grid moves along a trajectory that allows reducing Moire patterns during each exposure of a plurality of tomosynthesis exposures.

In some embodiments, the anti-scatter grid 104 may be retractable, either partially or fully, and/or decouplable so that it may be removed from the imaging area between the platform 112 and the X-ray detector 110 and/or the anti-scatter grid 104 can be swapped out for another grid having a different configuration. For example, the anti-scatter grid 104 may be retracted and/or decoupled outside the imaging area for operation in a 2D mammography mode and may be introduced back into the imaging area for operation in the tomosynthesis mode. Additionally and optionally, the anti-scatter grid 104 may be used in 2D mammography mode. Generally, for a multi-mode mammography system, the anti-scatter grid may be in the field of view for one mode, either stationary or moving during an exposure, and/or out of the field of view for another mode, e.g., in 2D mammography mode, magnification mode, etc. In various embodiments, the anti-scatter grid 104 may be configured according to one or more features disclosed herein, such as features described with reference to FIGS. 2 to 6.

Figures 2A, 2B, 2C:
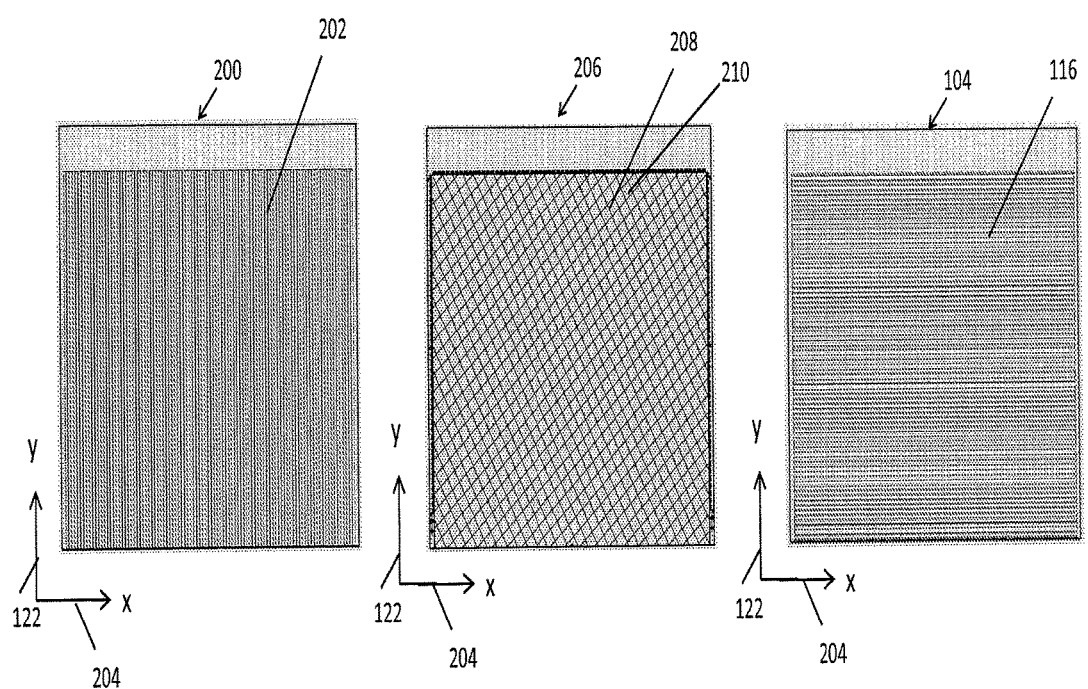
FIG. 2A is a top view of a conventional linear anti-scatter grid.
FIG. 2B is a top view of a conventional cellular anti-scatter grid.
FIG. 2C is a top view of the anti-scatter grid of FIG. 1 according to aspects of the present invention.

FIG. 2A is a top view of a conventional anti-scatter grid 200 having a plurality of septa 202. The septa 202 are linear and extend lengthwise parallel to the y-axis 122 shown in both FIGS. 1 and 2. The x-axis 204 shown in FIG. 2A is not visible in FIG. 1. When the anti-scatter grid 200 is used in conjunction with conventional 2D mammography systems, the septa 202 of the anti-scatter grid 200 are perpendicular to the coronal plane 126, in contrast with the configuration of the anti-scatter grid 104 wherein the septa 116 extend along a direction parallel to the coronal plane.

FIG. 2B is a top view of a conventional cellular anti-scatter grid 206 having a first series of septa 208 and a second series of septa 210 that extend perpendicular to the first series of septa. The septa 208 and 210 are oriented at a non-zero angle relative to the x-axis 204 and the y-axis 122, thereby creating a cross hatched pattern. Referring to FIGS. 2A and 2B, the conventional anti-scatter grids 200 and 206 are typically used in 2D mammography imaging systems. However, as described above, these conventional grids do not address the challenges associated with tomosynthesis imaging.

FIG. 2C shows a top view of the anti-scatter grid 104 illustrated and described above with reference to FIG. 1. FIG. 2C further illustrates the length of the septa 116. In FIG. 2C, the septa 116 are shown to extend lengthwise along the direction of the x-axis 204 (the x-axis is not visible in the cross-sectional view of FIG. 1). More generally, the septa 116 may extend lengthwise along the direction of any axis that is substantially parallel to the coronal plane 126 (or the x-z plane). Anti-scatter grids may be characterized by a septa density equal to $1/(d+t)$ where d is the distance between adjacent septa and t is the thickness of the septa. The septa density of the anti-scatter grid 104 of certain aspects is around 100 septa per cm. In other embodiments, the septa density may be at least 70 septa per cm, preferably about 100 septa per cm, in contrast with conventional anti-scatter grids which typically have septa densities in the range of 30 to 50 septa per cm. A higher septa density allows the anti-scatter grid to move a relatively short distance compared to conventional anti-scatter grids to reduce Moire patterns in the resulting images. This allows the use of the anti-scatter grid in tomosynthesis imaging systems which typically impose tight spatial constraints on the distance that the anti-scatter grid may move during imaging. It is to be noted that while the increased septa density of the anti-scatter grid 104 has advantages for tomosynthesis imaging as described above, the increased density of the septa and/or grid ratio, defined by $h/d$ where h is the septa height and d is the distance between septa, may also result in reduction of primary X-rays reaching the X-ray detector, which may necessitate delivering an increased radiation dose to the subject being imaged.

Figure 3A:
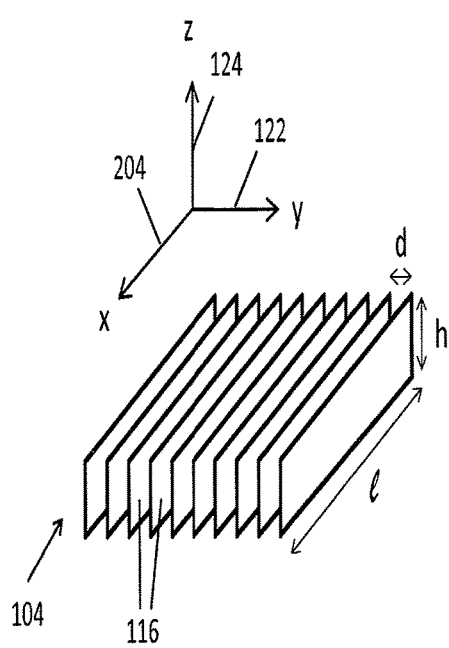
FIG. 3A is a perspective view of the anti-scatter grid of FIG. 1 according to aspects of the present invention.

FIG. 3A shows a perspective view of the anti-scatter grid 104 having a plurality of septa 116, further illustrating the orientation of the anti-scatter grid relative to the same reference frame defined by the orthogonal axes x, y and z of FIG. 1. The coronal plane 126 of FIG. 1 is parallel to the x-z plane including the x-axis 204 and the z-axis 124, and the sagittal plane of the subject 100 of FIG. 1 is parallel to the y-z plane including the y-axis 122 and the z-axis 124. Each septum 116 is a thin strip having a respective length l, height h and thickness t. Each septum 116 is shown in FIG. 3A to extend lengthwise along a respective axis that is parallel to the x-z plane or the coronal plane 126. Adjacent septa are separated by a distance d. The interspaces between the septa may include a low X-ray attenuating material. In some embodiments, the anti-scatter grid may include a support made of aluminum or another low X-ray attenuating material.

Figure 3B:
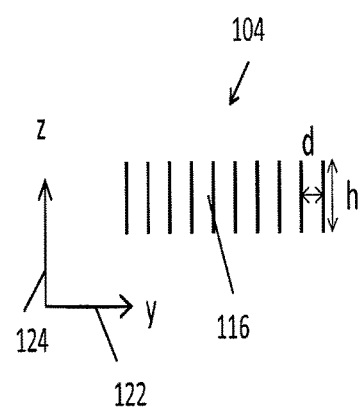
FIG. 3B is a side view illustrating a distance between adjacent septa of the anti-scatter grid of FIG. 1 according to aspects of the present invention.

FIG. 3B shows a side view of the anti-scatter grid 104 having septa 116, further illustrating the distance d between adjacent septa. In FIGS. 3A and 3B, the septa 116 of the anti-scatter grid 104 are shown to be arranged in a parallel configuration wherein the septa are parallel to each other. For example, FIG. 3A shows the plane defined by the length and height of each septum 116 being parallel to the planes of the other septa. In other embodiments, the anti-scatter grid may have septa that are arranged in a focused configuration, with the septa being substantially focused towards the focal spot of the X-ray source, such as the X-ray source 106 of FIG. 1. In this case, the planes defined by the height and length of the septa may not be parallel to each other, but instead may be slightly off-angle and oriented to match the divergence of the X-ray beams from the focal spot of the X-ray source to the X-ray detector. Focusing the septa of the anti-scatter grid allows the passage of primary X-rays along paths that emanate from the focal spot of X-ray source and blocks scattered X-rays that travel along other paths. During tomosynthesis imaging, an anti-scatter grid having septa arranged in a focused configuration may be moved to match the movement of the X-ray source such that the septa remain focused towards the focal spot of the X-ray source. It is to be appreciated that anti-scatter grids having focused septa may also have the septa extend lengthwise along a direction parallel to the coronal plane of the subject being imaged according to aspects of the present disclosure.

Figure 4A:
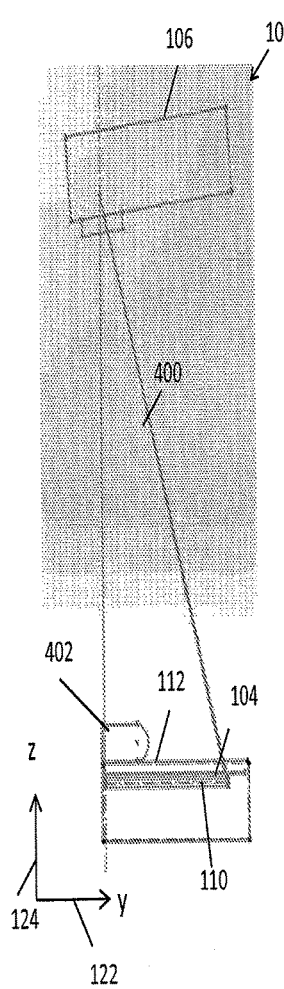
FIG. 4A is the cross-sectional view of the tomosynthesis imaging apparatus of FIG. 1, further illustrating a cone shaped X-ray beam according to aspects of the present invention.

FIG. 4A shows a cross-sectional side view of the tomosynthesis imaging apparatus 102 of FIG. 1, including the X-ray source 106, the X-ray detector 110, the platform 112 and the anti-scatter grid 104 positioned between the platform 112 and the X-ray detector 110. FIG. 4A further illustrates a conical shaped X-ray beam 400 emitted by the X-ray source 106 and transmitted through the compressed breast 402 (compressing structure not shown in FIG. 4A). As discussed above, the anti-scatter grid 104 may be configured such that the septa are arranged in a focused configuration to match the divergence of the X-ray beam 400 from the focal spot of the X-ray source 106 to the X-ray detector 110, taking into account for example the distance between the X-ray source and the anti-scatter grid.

Figure 4B:
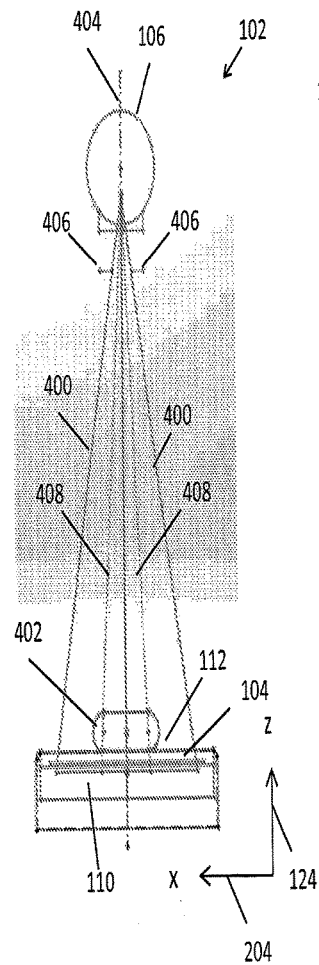
FIG. 4B is a front view of the tomosynthesis imaging apparatus of FIG. 1, illustrating a central position of the X-ray source according to aspects of the present invention.

FIG. 4B is a front view of the tomosynthesis imaging apparatus 102 of FIGS. 1 and 4A, further illustrating the X-ray source 106 being positioned above the compressed breast 402 and aligned with a central axis 404. The X-ray detector 110 and the anti-scatter grid 104 are oriented parallel to the x-y plane (or the transverse plane 128 of FIG. 1). The anti-scatter grid 104 has septa that extend lengthwise along a direction parallel to the x-z plane (or the coronal plane 126 of FIG. 1). The septa may further be focused towards the focal spot of the X-ray source 106. FIG. 4B further illustrates a collimator 406 of the tomosynthesis imaging apparatus 102. The collimator 406 is positioned between the X-ray source 106 and the platform 112 and configured to restrict the X-ray beam 400, resulting in a restricted X-ray beam 408 so as to irradiate only the breast 402 to be imaged. Using the collimator 406 avoids irradiating portions of the subject that are not being imaged, and further reduces the contribution of Compton-scattered. X-rays to the resulting image.

Figure 4C:
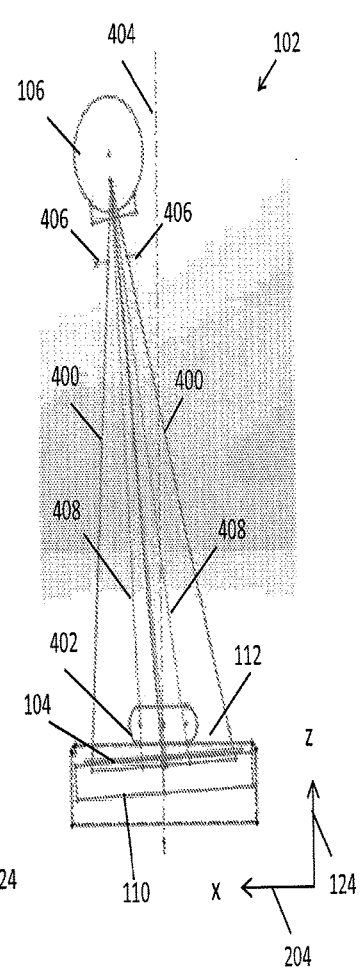
FIG. 4C is a front view of the tomosynthesis imaging apparatus of FIG. 1, further illustrating a movement of the X-ray source, and reciprocal movement of the X-ray detector and the anti-scatter grid according to aspects of the present invention.

FIG. 4C is a front view of the tomosynthesis imaging apparatus 102 of FIGS. 1, 4A and 4B, further illustrating movement of the X-ray source 106 and reciprocal movement of the X-ray detector 110 and the anti-scatter grid 104. When the tomosynthesis imaging apparatus 102 is operating in 2D mammography mode, the X-ray source 106 is stationary and an image corresponding to the fixed position of the X-ray source, such as the position aligned with the central axis 404 of FIG. 4B, is obtained. When the tomosynthesis imaging apparatus 102 is operating in the tomosynthesis mode, multiple X-ray images are taken as the X-ray source 106 and the X-ray detector 110 move relative to the immobilized and compressed breast 402. FIG. 4C shows the X-ray source 106 positioned at an angle relative to the central axis 404. FIG. 4C further shows that the X-ray detector 110 and the anti-scatter grid 104 are rotated around the central axis 404 so as to remain oriented towards the X-ray source 106. The septa of the anti-scatter 104 may remain substantially parallel to the x-z plane (or coronal plane 126) as the anti-scatter grid moves along with the X-ray detector 110. In addition to the motion of the anti-scatter grid that is coupled to the motion of the X-ray detector 110, the anti-scatter grid 104 may further move relative to the X-ray detector as described and illustrated for example with reference to FIG. 1B. In some embodiments, the anti-scatter grid 104 may rotate with the X-ray detector 110 and may translate relative to the X-ray detector. For example, the X-ray detector 110 may rotate to match different angular positions of the X-ray source 106 between X-ray exposures and may move relative to the X-ray detector to reduce Moire patterns during each X-ray exposure for tomosynthesis imaging. In other embodiments, the anti-scatter grid need not move in conjunction with the X-ray detector during tomosynthesis imaging. For example, the anti-scatter grid may remain stationary, or may move at a different rate than the X-ray detector, or may move in a different direction than the X-ray detector.

While only a single off-center position of the X-ray source 106 is illustrated in FIG. 4C, in practice image data is taken at each of a much greater number of positions of the X-ray source 106, for example, at every 1° of an arc that extends from −15° to +15° relative to the central axis 404. In some embodiments, the taking of image data may occur while the X-ray source 106, the anti-scatter grid 104 and the X-ray detector 110 are stopped at their respective positions, after moving from one position to the next. That is, at each position corresponding to the X-ray source 106, the anti-scatter grid 104 and the X-ray detector 110, the X-ray source 106 is energized to emit a collimated X-ray beam to obtain a respective image of the breast 402. In other embodiments, the motion of one or all of X-ray source 106, the X-ray detector 110 and the anti-scatter grid 104 may be continuous, with a respective set of image data being accumulated over a small increment of continuous motion, for example a 0.1° to 0.5° arc of motion of the X-ray source 106. Furthermore, while FIG. 4C illustrates rotation of the X-ray detector 110 to maintain its orientation towards the X-ray source 106, in other embodiments, the X-ray detector may move linearly, for example while remaining parallel and at the same distance from the platform 112. In still other embodiments, the X-ray detector 110 rotates in the same direction as the X-ray source 106. Rotation of the X-ray detector 110 is both synchronous and angularly proportionate to the X-ray source 106. During tomosynthesis, the X-ray detector 110 may rotate at a fractional rate of 1/3.5, i.e. ±4.3°, for X-ray source 106 rotation of ±15°. The X-ray source 106 is driven and the X-ray detector 110 follows through a gear mechanism. In other embodiments, movement of the X-ray source 106 and detector 110 may be coordinated via a controller, as in the system described below in FIG. 8.

The systems described herein enable movement of an anti-scatter grid relative to either or both of an X-ray source and an X-ray detector. For example, with reference to FIGS. 1A and 1B, the anti-scatter grid 116 may move along an axis parallel to the z-axis 124 (i.e., closer to or further from the X-ray source 106). In another embodiment, the anti-scatter grid 116 may move along an axis parallel to the y-axis 122 (i.e., closer to or further from the patient 100). Alternatively or additionally, the anti-scatter grid 116 may move along an axis parallel to the x-axis (not shown) (i.e., side-to-side, relative to the patient 100). Pivoting movement, for example, about the y-axis as depicted in FIG. 4C above, or about the x-axis, is also contemplated. Rotational movement about the central axis 404 depicted in FIG. 4B may also be utilized if desired.

Exemplary systems and structures that enable movement relative to particular planes or axes are described in further detail below. Movement of an anti-scatter grid along certain axes can display particularly desirable results when used in conjunction with tomosynthesis. Although a single motor is depicted in the following examples, multiple motors or actuators may be used in conjunction with an anti-scatter grid to move that element in any direction, as required or desired for a particular application. Additionally, a motor may drive a linkage or other element having multiple degrees of freedom to move the anti-scatter grid as desired relative to any plane or axis defined herein. Gears systems may be utilized to control rates of movement relative to either or both of the detector and the emitter.

Figure 5:
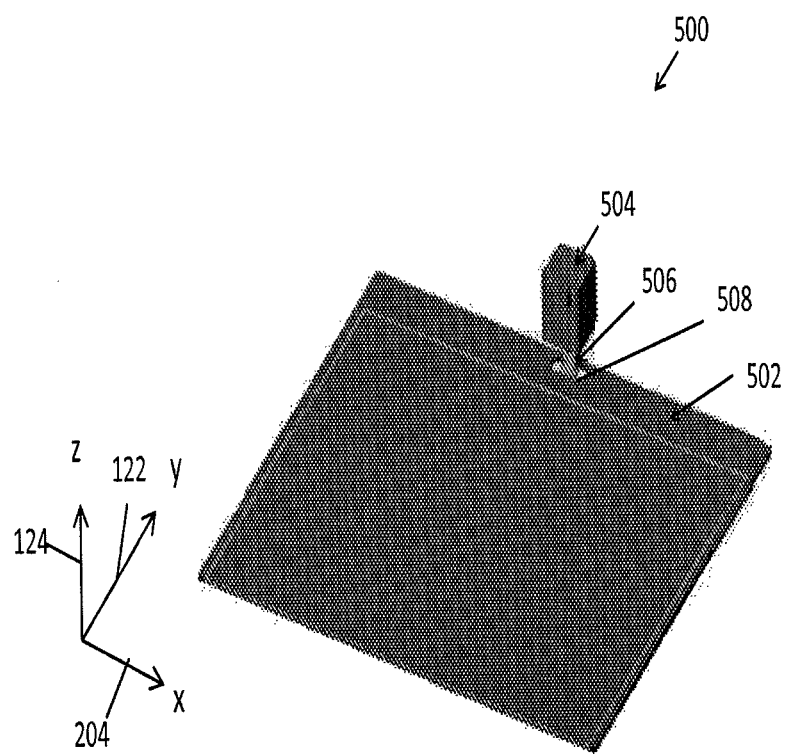
FIG. 5 is a perspective view of one embodiment of an apparatus for reducing X-ray scatter according to aspects of the present invention.

FIG. 5 is a perspective view of one embodiment of an apparatus 500 for reducing X-ray scatter. The apparatus 500 includes an anti-scatter grid 502 which may be configured according to one or more features disclosed herein. For example, the anti-scatter grid may have a plurality of septa wherein each septum extends lengthwise along a direction parallel to the x-z plane (or the coronal plane 126 of FIG. 1). The apparatus 500 further includes a motor 504. In some embodiments, the motor 504 may be a stepper motor or a servo motor. An eccentric 506 is coupled to the motor 504 at an off-center position. Furthermore, the anti-scatter grid 502 includes an elongated opening 508. The elongated opening 508 is elongated along a direction substantially parallel to the length of the septa. The eccentric 506 is inserted through the elongated slot 508. Since the opening 508 is elongated, at least one gap is created as the eccentric 506 is inserted through the elongated slot 508. As the eccentric 506 rotates, the anti-scatter grid 502 moves back and forth along a direction substantially parallel to the y-z plane (or parallel to the sagittal plane of FIG. 1). In this case, the anti-scatter grid 502 will move back and forth along the direction of the y-axis 122. The gap created as the eccentric 506 is inserted through the elongated slot 508 prevents the anti-scatter grid from moving along the direction of the x-axis 204. However, in other embodiments, the motor 504 may be coupled to the anti-scatter grid 502 so as to allow motion along the x-axis 204. Motors that utilize an eccentric connected to an anti-scatter grid may be oriented as desired to move the anti-scatter grid in any desired direction, relative to any plane or axis described herein.

A rotary motor such as the motor 504 of FIG. 5 may be used to provide a sinusoidal velocity profile. In various embodiments, the constant velocity of a rotary motor shaft may produce a sinusoidal profile, for example in the direction of the x-axis and/or the y-axis. In various embodiments, a rotary stepper motor may be a cost effective mechanism for providing a sinusoidal profile.

In one embodiment, the anti-scatter grid 104 of FIG. 1 may be configured according to the apparatus 500 and the anti-scatter grid 502 of FIG. 5. Thus, the anti-scatter grid 502 may be configured to move along a first direction substantially parallel to the sagittal plane of the subject 100 and may further be configured to move along a second direction substantially parallel to the coronal plane 126 of FIG. 1.

Figure 6:
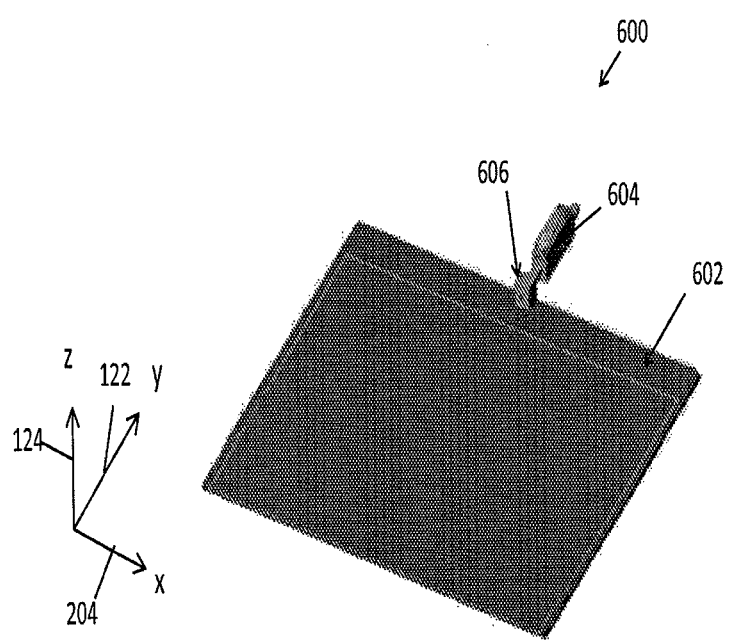
FIG. 6 is a perspective view of another embodiment of an apparatus for reducing X-ray scatter according to aspects of the present invention.

FIG. 6 is a perspective view of another embodiment of an apparatus 600 for reducing X-ray scatter. The apparatus 600 includes an anti-scatter grid 602 which may be configured according to one or more features disclosed herein. The apparatus 600 further includes a motor 604 coupled to the anti-scatter grid by a mechanism 606. In various embodiments, the motor 604 may be a linear motor, a stepper motor, a piezo-electric motor or a voice coil. The motor 604 may be configured to translate the anti-scatter grid back and forth along a direction, such as a direction parallel to the sagittal plane of the subject 100 in FIG. 1. In certain embodiments, this direction may be parallel to the y-axis 122. In various embodiments, a linear motor such as the motor 604 of FIG. 6 may be used to provide a trapezoidal profile, which may be more effective at blurring grid lines compared to a sinusoidal profile. However, a linear motor may be more expensive compared to a rotary motor. Regardless of the type of motor utilized, such motor may be connected to the anti-scatter grid as desired to move the anti-scatter grid in any desired direction, relative to any plane or axis described herein.

In various embodiments, the motor (such as the motor 504 of FIG. 5 or the motor 604 of FIG. 6) may be configured to move the anti-scatter grid with a velocity profile that is one of a sinusoidal profile and a trapezoidal profile and may be synchronized with the X-ray exposure durations of the tomosynthesis imaging mode. As described above with reference to FIGS. 5 and 6, a sinusoidal profile may be easier and more cost effective to implement, for example by using a rotary motor as shown in FIG. 5. A trapezoidal profile may be more expensive to implement, for example by using a linear motor as shown in FIG. 6. However, a trapezoidal profile may more effectively reduce Moire patterns compared to a sinusoidal profile.

Figure 7:
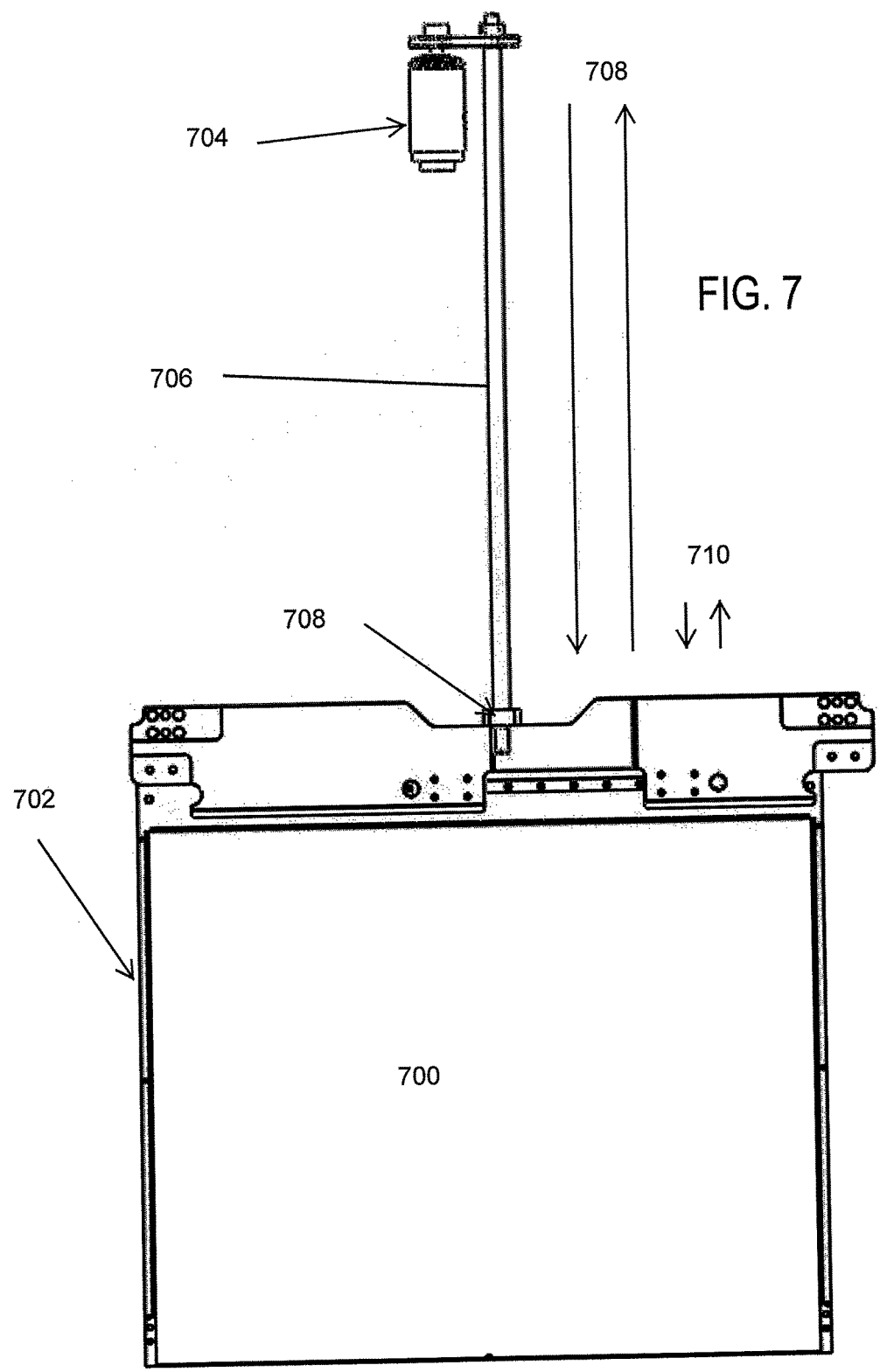
FIG. 7 is a plan view of yet another embodiment of an apparatus for reducing X-ray scatter according to aspects of the present invention.

FIG. 7 illustrates an embodiment of the present invention in which the motor that retracts an anti-scatter grid for a mammography system, e.g., an integrated, multi-mode mammography system, is the same motor that imparts motion to the anti-scatter grid during an exposure for tomosynthesis image acquisition. An anti-scatter grid 700 (septa not shown) is coupled to a grid carriage 702. The anti-scatter grid 700 and grid carriage 702 are coupled to a motor 704. One nonlimiting example of such a coupling includes a lead screw 706 that is coupled to the grid carriage 702 via a nut 708. Other known mechanical arrangements for coupling the motor 704 to the grid carriage 706 can be utilized. As discussed herein, in one mode 708, the motor 704 can fully retract the anti-scatter grid 700 out of the field of view. Alternatively, the motor 704 can partially retract the anti-scatter grid 700 so that it is not entirely in the field of view during an exposure. In another mode 708, the motor moves the anti-scatter grid 700 during an exposure for image acquisition, such as tomosynthesis image acquisition.

Figure 8:
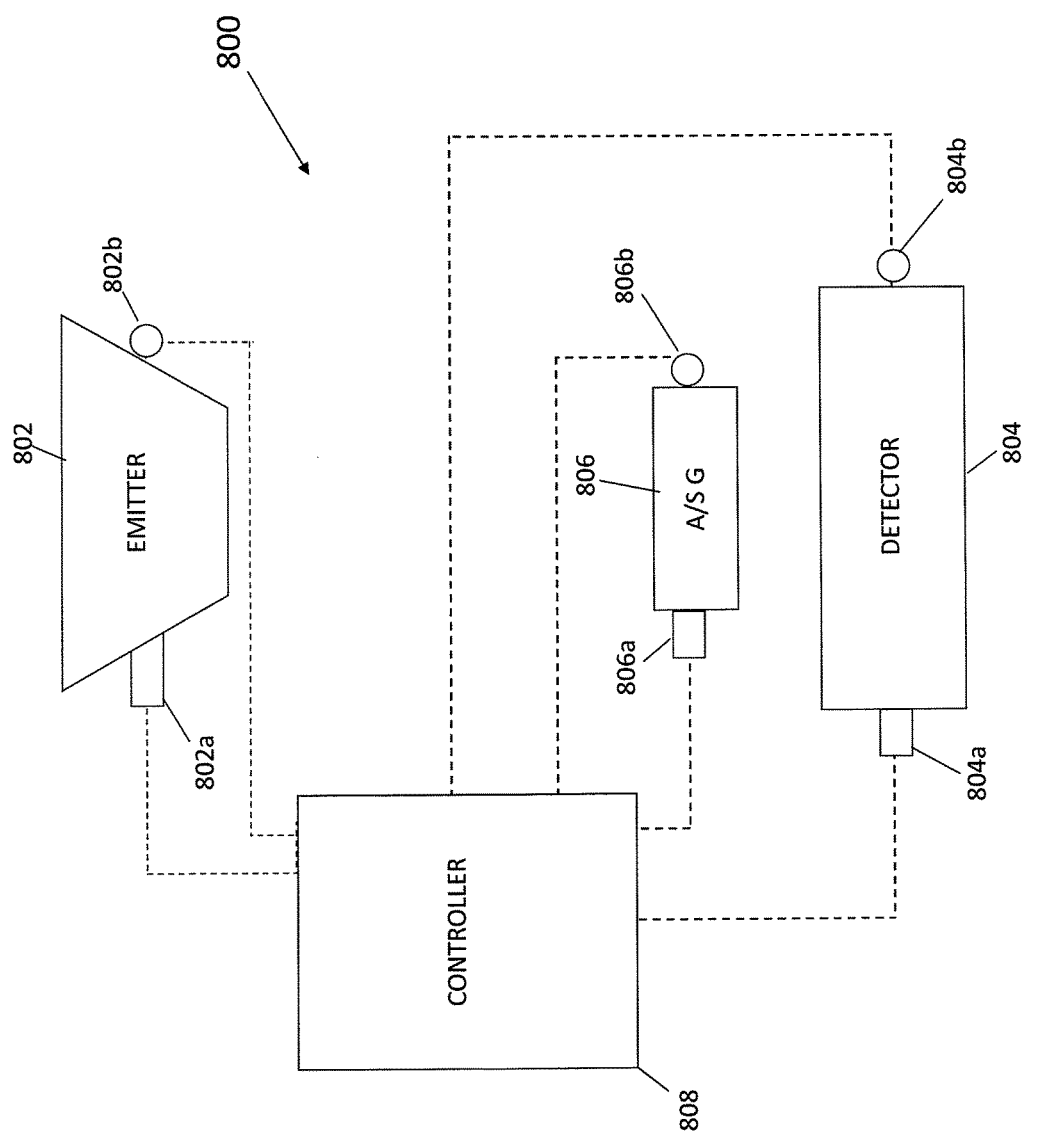
FIG. 8 depicts a system for reducing X-ray scatter in a tomosynthesis system.

FIG. 8 depicts a system for reducing X-ray scatter in a tomosynthesis imaging system 800. The system includes an X-ray emitter 802, a detector 804, and an anti-scatter grid 806. Each of these components includes a position sensor 802a, 804a, 806a, respectively. Additionally, each components may be actuated (e.g., moved linearly, rotatably, pivotally, etc.) by one or more actuators or motors 802b, 804b, 806b, respectively. Signals indicative of position, orientation, rate of movement, etc., are sent to a controller 808 that can actuate any of the three components 802, 804, 806. Thus, the controller determines the position of each component relative to one or more of the other components, and sends signals to the various actuators to move each component as required or desired.

Figure 9:
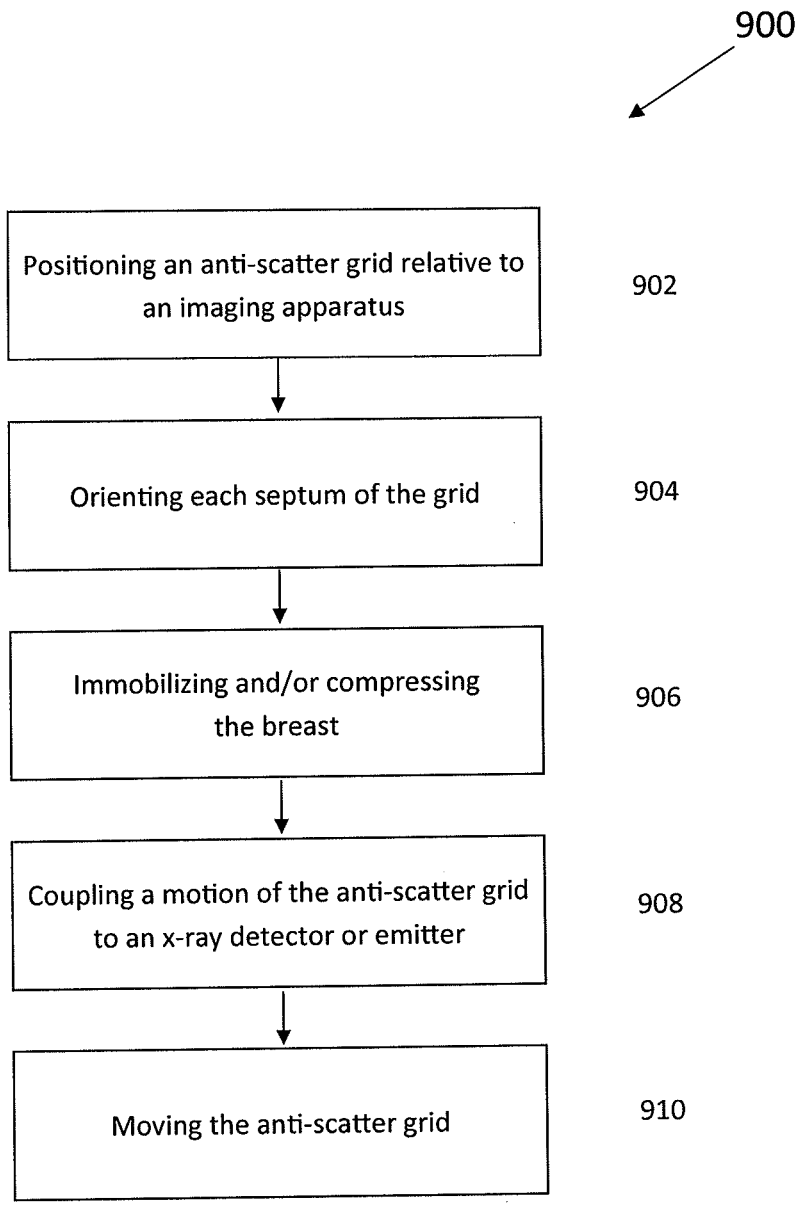
FIG. 9 depicts a method of reducing X-ray scatter in a tomosynthesis system.

FIG. 9 depicts a method of reducing X-ray scatter 900 in a tomosynthesis system. In the depicted embodiment, a method of reducing X-ray scatter 900 may comprise positioning an anti-scatter grid configured according to one or more features disclosed herein relative to an X-ray imaging apparatus, such as a tomosynthesis imaging device. In particular, the method may include positioning the anti-scatter grid between an X-ray source and an X-ray detector (operation 902) of the tomosynthesis imaging apparatus, as shown for example in FIGS. 1 and 4. The method may further include orienting each septum of a plurality of septa of the anti-scatter grid (operation 904) lengthwise along a respective axis that is substantially parallel to a coronal plane of the subject during tomosynthesis imaging of the breast, as illustrated and described above with reference to FIGS. 1 to 4. In some embodiments, the anti-scatter grid may have a septa density of at least 70 septa per cm. The septa may be arranged in a parallel configuration or a focused configuration relative to the X-ray source.

In some embodiments, the method may further include at least one of immobilizing and compressing the breast of the subject (operation 906), for example using an immobilization or compression structure as shown in FIG. 1.

In various embodiments, the method of reducing X-ray scatter may also encompass reducing a Moire pattern in a resulting image. Thus, the method of reducing X-ray scatter may further comprise coupling a motion of the anti-scatter to that of the X-ray detector or emitter (operation 908) such that the anti-scatter grid moves with the X-ray detector or emitter during tomosynthesis imaging. Once coupled, the anti-scatter grid may be moved (operation 910) relative to either or both of the X-ray emitter or detector. In various embodiments, moving the anti-scatter grid may include rotating or translating the anti-scatter grid. In some embodiments, the method may include moving the anti-scatter grid along a first direction that is substantially parallel to a sagittal plane of the subject during tomosynthesis imaging, as shown for example in FIG. 1B. In some embodiments, the method may include moving the anti-scatter grid in a second direction that is substantially parallel to a coronal plane of the subject during tomosynthesis imaging. In various embodiments, moving the anti-scatter grid may include moving the anti-scatter grid at a velocity effective to reduce a Moire pattern in a resulting image. For example, the velocity profile may be one of a trapezoidal profile and a sinusoidal profile. Using anti-scatter grids with a relatively high septa density compared to conventional anti-scatter grids will further allow the anti-scatter grid to effectively reduce Moire patterns while moving only a small distance within the confines of the tomosynthesis imaging apparatus during each X-ray exposure.

In various embodiments, the X-ray imaging apparatus may be an integrated mammography and tomosynthesis apparatus configured to be operable in both 2D and 3D modes. In some embodiments, the method of reducing X-ray scatter may include using the same anti-scatter grid configured according to aspects disclosed herein for imaging in both 2D and 3D modes. In other embodiments, the method may include retracting the anti-scatter grid configured according to aspects disclosed herein or switching the anti-scatter grid with a conventional anti-scatter grid for imaging in the 2D mammography mode.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only, and the scope of the disclosure should be determined from proper construction of the appended claims, and their equivalents.

What is claimed is:

1. An apparatus for reducing X-ray scatter, the apparatus comprising:
a motor; and
an anti-scatter grid coupled to the motor, the anti-scatter grid having a plurality of septa, and the anti-scatter grid being configured to be positioned relative to an X-ray imaging device such that each septum of the plurality of septa extends along a direction substantially parallel to a coronal plane of a subject during imaging of the subject using the X-ray imaging device,
wherein the motor is configured to retract the anti-scatter grid out of the field of view in a first mode of the X-ray imaging device and the motor is configured to move the anti-scatter grid relative to a detector in the field of view in a second mode of the X-ray imaging device,
wherein the detector is configured to rotate during imaging in the second mode, and wherein the anti-scatter grid is configured to move in a corresponding rotational direction with the detector during imaging in the second mode.

2. The apparatus of claim 1, wherein the X-ray imaging device is a tomosynthesis imaging device.

3. The apparatus of claim 2, wherein the X-ray imaging device is configured to operate in a 2D mammography mode and a 3D tomosynthesis mode.

4. The apparatus of claim 1, wherein the anti-scatter grid is further configured to move along a first direction substantially parallel to a sagittal plane of the subject during imaging of the subject using the X-ray imaging device.

5. The apparatus of claim 4, wherein the anti-scatter grid is further configured to move along a second direction substantially parallel to the coronal plane of the subject during imaging of the subject using the X-ray imaging device.

6. The apparatus of claim 1, wherein the anti-scatter grid is further configured to move along a trajectory and at a velocity effective to reduce a Moire pattern in a resulting image during imaging of the subject using the X-ray imaging device operating in a tomosynthesis mode.

7. The apparatus of claim 6, wherein the anti-scatter grid is further configured to move along the trajectory during each exposure of a plurality of tomosynthesis exposures.

8. The apparatus of claim 6, wherein the anti-scatter grid has a density of at least 70 septa per cm to confine a distance of motion required to reduce the Moire pattern.

9. The apparatus of claim 1, wherein the motor is a first motor and the apparatus further comprising:
a second motor coupled to the anti-scatter grid and configured to move the anti-scatter grid during imaging of a breast of the subject using the X-ray imaging device operating in a tomosynthesis mode.

10. The apparatus of claim 9, wherein the second motor is further configured to move the anti-scatter grid along a first direction substantially parallel to a sagittal plane of the subject during imaging of the breast using the X-ray imaging device operating in the tomosynthesis mode.

11. The apparatus of claim 9, wherein the second motor is further configured to move the anti-scatter grid with a velocity profile that is one of a trapezoidal profile and a sinusoidal profile.

12. An apparatus configured to operate in a tomosynthesis mode for imaging of a breast of a subject, the apparatus comprising:
a motor;
an X-ray source configured to move for imaging in the tomosynthesis mode;
an X-ray detector configured to move in a reciprocal direction relative to a motion of the X-ray source during imaging in the tomosynthesis mode;
a platform configured to position the breast between the X-ray source and the X-ray detector; and
an anti-scatter grid disposed between the platform and the X-ray detector, the anti-scatter grid having a plurality of septa, each septum of the plurality of septa having a length extending along a direction substantially parallel to a coronal plane of the subject, wherein the anti-scatter grid is configured to move in a corresponding rotational direction with the detector during imaging in the tomosynthesis mode, and wherein the motor is configured to retract the anti-scatter grid out of the field of view in a first mode of the apparatus and the motor is configured to move the anti-scatter grid relative to the X-ray detector in the field of view in a second mode of the apparatus, the second mode being the tomosynthesis mode.

13. The apparatus of claim 12, wherein the anti-scatter grid is configured to move along a first direction substantially parallel to a sagittal plane of the subject during imaging in the tomosynthesis mode.

14. The apparatus of claim 13, wherein the anti-scatter grid is further configured to move along a second direction substantially parallel to the coronal plane of the subject during imaging in the tomosynthesis mode.

15. The apparatus of claim 12, wherein the anti-scatter grid is further configured to move along a trajectory and at a velocity effective to reduce a Moire pattern in a resulting image during imaging in the tomosynthesis mode.

16. The apparatus of claim 15, wherein the anti-scatter grid is further configured to move along the trajectory during each exposure of a plurality of tomosynthesis exposures.

17. The apparatus of claim 12, wherein the motor is further configured to move the anti-scatter grid with a velocity profile that is one of a trapezoidal profile and a sinusoidal profile.

18. The apparatus of claim 12, wherein the plurality of septa are arranged in a parallel configuration.

* * * * *